US 6,660,713 B2

(12) United States Patent
Carter et al.

(10) Patent No.: US 6,660,713 B2
(45) Date of Patent: Dec. 9, 2003

(54) HYDROPHOBIC NANOZEOLITES FOR MALODOR CONTROL

(75) Inventors: John David Carter, Newcastle-Upon-Tyne (GB); Robert Corkery, Cincinnati, OH (US); Jun Ma, Jiangsu (CN); Robert Henry Rohrbaugh, Indian Springs, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/772,742

(22) Filed: Jan. 30, 2001

(65) Prior Publication Data

US 2002/0142937 A1 Oct. 3, 2002

(51) Int. Cl.⁷ .................................................. C11D 3/08
(52) U.S. Cl. ........................ 510/507; 510/276; 510/278; 510/315; 510/323; 510/377; 510/532
(58) Field of Search ................... 510/276, 278, 510/315, 323, 377, 507, 532

(56) References Cited

U.S. PATENT DOCUMENTS

| 4,265,777 | A | * | 5/1981 | Boyer et al. | 252/113 |
|---|---|---|---|---|---|
| 4,269,725 | A | * | 5/1981 | Smith et al. | 252/174.25 |
| 4,493,781 | A | * | 1/1985 | Chapman et al. | 252/88 |
| 5,084,427 | A | * | 1/1992 | Tsoucalas | 502/62 |
| 5,184,630 | A | * | 2/1993 | Jung | 132/202 |
| 5,582,819 | A | * | 12/1996 | Shul et al. | 423/705 |
| 5,744,404 | A | * | 4/1998 | Titterton et al. | 442/63 |
| 5,863,516 | A | | 1/1999 | Otterstedt et al. | |
| 5,871,650 | A | | 2/1999 | Lai et al. | |
| 5,939,060 | A | | 8/1999 | Trinh et al. | |
| 6,106,738 | A | | 8/2000 | Woo et al. | |

FOREIGN PATENT DOCUMENTS

| GB | 2 296 261 A | 6/1996 |
|---|---|---|
| WO | WO 9308125 | 4/1993 |
| WO | WO 9317661 | 9/1993 |
| WO | WO 00/51940 | 9/2000 |

* cited by examiner

*Primary Examiner*—Charles Boyer
(74) *Attorney, Agent, or Firm*—Dinsmore & Shohl LLP

(57) ABSTRACT

Cleaning and deodorizing compositions comprising hydrophobic, nanozeolites for odor control on substrates are disclosed. Specifically, cleaning and deodorizing compositions for malodor control comprising nanozeolites and methods for removing odors from substrates using said compositions are disclosed.

27 Claims, No Drawings

HYDROPHOBIC NANOZEOLITES FOR MALODOR CONTROL

FIELD OF THE INVENTION

This invention relates to cleaning and deodorizing compositions comprising hydrophobic, nanozeolites for odor control on substrates. Specifically, this invention is related to cleaning and deodorizing compositions for malodor control comprising nanozeolites and methods for removing odors from substrates using said compositions.

BACKGROUND OF THE INVENTION

The suppression or elimination of odors, particularly undesirable odors, has been the objective of countless investigations. Malodors originate from many sources but those that are of most consequence to human beings are those involving occasional or repeated daily exposure. As a consequence of normal daily activity, various substrates including fabrics, upholstery, carpeting, and other substrates (i.e. pets) are exposed to a variety of malodors, some of which are produced by humans, as in the case of perspiration, and some are environmentally generated malodors (e.g. cigarette smoke).

Cultural and aesthetic standards have influenced the permissible level of human and environmental malodors and control of these odors has been the focus of investigation for many centuries. In general, these investigations have been focused on either of two approaches, namely (a) odor masking, in which a substance of strong yet relatively pleasant odor is introduced into the proximity of a less pleasant odor source with the intent of overburdening the olfactory receptors with the dominant pleasant odor, or (b) sequestering the undesired odorous substance in a non-volatile form either by chemical reaction, adsorption or absorption on a sorbent material exhibiting a sorptive preference for the odorous substance. One additional approach that has been investigated is preventing the formation of the odors altogether.

Odor masking, although effective in the short term, has certain limitations. First, masking does not remove or eliminate the source of the malodor. Secondly, when scents and perfumes are used to overcome malodors, the user must make sure an effective and constant level of masking agent is present to avoid too low a level of masking agent that may not be sufficient to cover-up the malodor. In turn, too high a level of masking agent may itself produce an undesirable effect. The premature depletion of the masking agent can be an additional concern.

Sequestration has thus become the method of choice for elimination and control of both human and environmental malodors. The more effective approach has been to sequester the undesired malodor primarily by adsorption.

By far the most commonly employed of the solid adsorbents is activated charcoal or active carbon, although silica gel, activated alumina, kieselguhr, Fullers earth and other clay minerals and zeolites, alone or in combination, have also been proposed as odor "adsorbents". In U.S. Pat. No. 4,437,429, the use of a hydrated zeolite in admixture with clay is proposed as being particularly useful for the control of odors from pet litter. Though it is observed that the use of zeolites by themselves as litter material has generally been unsuccessful due to their poor water adsorption properties as compared with clays. The best remedy for substrate malodor remains the effective sequestering of malodorous molecules as they are either formed or come into contact with the substrate.

The desire to provide a laundry detergent that provides laundered substrates with malodor control that does not involve masking the malodors with perfumes, led to the investigation of adsorbents, chelants and other odor control agents. Activated charcoal, one of the most efficient adsorptive materials, along with finely divided aluminosilicate adsorbents and clays, have been excluded from use because they are either not compatible with substrate color (i.e. black charcoal on white clothing or white zeolite powder on dark clothing) or they are not compatible with the aqueous delivery system normally associated with laundry detergents.

Compounds such as cyclodextrin, have also recently been used as odor adsorbents because of their ability to bind a variety of odors in their "hydrophobic" cavity. Nevertheless, because the pores of cyclodextrin are relatively large, many small molecules, especially those bearing thiol, sulfide or amine functionality are not bound effectively by cyclodextrin, necessitating the use of odor control adjuvants such as polyacrylic acid. In addition, odor control with cyclodextrin is only possible in the wet state, not in the dry state. This is a result of the fact that odor molecules must first transition into the aqueous phase before being adsorbed by the cyclodextrin molecule. This places unwanted limitations on its uses as an odor control agent.

Aluminosilicates in the form of microporous zeolites have long been of value in laundry detergent compositions as builders. They serve in general as ion exchange agents whose primary function is to remove calcium and magnesium ions from the laundry wash liquor and replace them with sodium, potassium or other suitable cations that do not decrease the surface activity of laundry detergent surfactants. The use of zeolites for adsorption of malodors, however, is limited by the fact that traditional zeolites leave a white residue on substrates treated with them.

Adsorption, and hence the sequestration, of odors such as ammonia as described in U.S. Pat. No. 5,013,335 is accomplished by zeolitic material where selected synthesis and calcination affords porous molecular sieves with a pore size large enough to accommodate ammonia molecules. However, when applied to adsorption of molecules typically responsible for malodor, these common microporous zeolites fail in several ways. The surface of high aluminum containing zeolites have an abundance of bound cations and together with the associated "water of hydration" produce a hydrophilic surface barrier not compatible with the adsorption mechanism associated with the diffusion of larger, non-polar, non-charged organic species at the solid/air interface.

It is desirable to be able to apply a uniform coating of a malodor control agent to the entire substrate, which provides removal of odors already present on the substrate as well as preventing new environmental odors from attaching to the substrate.

Therefore, the need still remains for an effective malodor control composition which can be uniformly applied to a substrate, remains invisible to the naked eye and has the ability to adsorb/remove a broad range of consumer relevant odors. There is additionally a need for a composition, which can deliver a strong/irreversible adsorption of malodor in both the wet and dry states to provide removal of odors and prevent initial deposition of odor molecules on substrates.

SUMMARY OF THE INVENTION

It has now been surprisingly discovered that cleaning and deodorizing compositions comprising nanozeolites effectively control malodor on substrates. These nanozeolites may be delivered via inclusion in a detergent composition during a laundry wash process, or may be directly applied to substrates (e.g., by spraying on the substrate in need of malodor control).

The present invention relates to laundry detergent compositions comprising nanozeolites for control of malodorous compounds that come into contact with a substrate in the course of normal usage. The nanozeolites useful in the present invention have at least one pore system with pore sizes from about 3 to about 12 angstroms.

The compositions of the present invention when practiced in the area of laundry detergent compositions will optionally comprise, detersive surfactants, builders, buffers, bleaching compounds, bleach activators, chelating agents, anti-redeposition agents, dispersents, brightners, suds suppressers, hydrotropes, soil release agents, fabric softeners, filler salts, and mixtures thereof, in addition to the nanozeolites. Compositions of the present invention therefore preferably comprises from about 1% to about 99% of such adjunct ingredients.

In an alternative embodiment of the present invention the composition comprises from about 0.05% to about 10% by weight of a nanozeolite, from about 90% to about 99.95% by weight of a liquid carrier, and optionally additional ingredients selected from the group consisting of surfactants, perfumes, preservatives and other conventional detergent ingredients. In a preferred embodiment of the present invention the composition is free of any material that would soil or stain the substrate.

The nanozeolites of the present invention have a silica to alumina molar ratio of at least 10:1, preferably of at least 60:1, more preferably of at least 100:1. The cleaning and deodorizing compositions of the present invention can comprise nanozeolites of more than one particle size, that is, the same composition can comprise a range of particle sizes as long as at least 50% are less than 300 nm. The nanozeolites suitable for use in the present invention may be present as discrete particles or as aggregates of discrete particles as long as the aggregates have an overall particle size of less than 300 nm.

The nanozeolites of the present invention may be calcined or uncalcined. Preferably the nanozeolites have an overall particle size (discrete or aggregated), of less than 300 nm, more preferably less than 200 nm and most preferably less than 100 nm.

The present invention also relates to a method of controlling substrate malodor by applying to a substrate a composition containing nanozeolites. Subsequent exposure of said substrate to malodors, whether the malodors are created either by the user (i.e. perspiration) or the malodors are environmental (i.e. cigarette smoke), results in a decreased level of malodor present on said substrate after the source of malodor has been removed. This method of the present invention to control malodor on substrate may involve either contacting said substrate with a laundry detergent or a substrate treatment composition comprising nanozeolites described further herein.

One object of the present invention is the adsorption of a wide variety of malodors on substrates. Another object of the present invention is the delivery of an invisible malodor control composition to substrates. The delivery of an effective, widely applicable malodor control agent via the laundering process is an additional object of the present invention.

All percentages, ratios and proportions are by weight, unless otherwise specified. All documents cited are incorporated herein by reference in their entirety.

DETAILED DESCRIPTION OF THE INVENTION

The present invention relates to compositions and methods for controlling malodor on substrates. The malodor control composition can be delivered in a variety of ways including but not limited to inclusion in detersive laundry compositions or, alternatively, as a substrate treatment composition applied directly to the substrate. A substrate treatment composition of the present invention comprises nanozeolites, a suitable carrier and, optionally, perfumes and other compatible detergent ingredients.

Discrete particles and/or aggregates less than 300 nm in diameter, can be applied to a variety of substrates without the visual negatives commonly associated with inorganic particulates and activated carbon. Specifically, colloidal silicalite, a hydrophobic zeolite belonging to the same structural class as ZSM-5, can be sprayed on dark substrates without any apparent whitening. Furthermore, uniformity of resulting thin film is much improved versus the equivalent micron sized particulates.

The present invention is more specifically directed to compositions for removing and controlling malodor on substrates. One such composition comprises:

(A) from about 0.05% to about 10% by weight of nanozeolite;

(B) from about 90% to about 99.95% by weight of a compatible carrier; and (C) optionally additional ingredients selected from the group consisting of surfactants, perfumes, preservatives, anti-microbials, de-foaming agents, anti-foaming agents, bacteriocides, fungicides, antistatic agents, insect and moth repellents, colorants, bluing agents, antioxidants and mixtures thereof. Preferably the composition is free of any material that would soil or stain the substrate.

The present invention is also directed to a method for removing malodor from a porous substrate, the method comprising the steps of:

(A) applying a uniform layer to a substrate, of a composition comprising:
  (i) from about 0.05% to about 10% by weight of nanozeolite;
  (ii) from about 90% to about 99.95% by weight of a liquid carrier; and
  (iii) optionally additional ingredients selected from the group consisting of surfactants, perfumes, preservatives, anti-microbials, de-foaming agents, antifoaming agents, bacteriocides, fungicides, antistatic agents, insect and moth repellents, colorants, bluing agents, antioxidants and mixtures thereof; and (B) allowing the substrate to dry. Preferably the composition is free of any material that would soil or stain the substrate. In the above described method the malodor control composition can be applied to the substrate either by spraying with a liquid composition comprising the nanozeolites or washing the substrate with a laundry detergent composition comprising the nanozeolites.

The present invention is also directed to a laundry detergent composition comprising:

(i) from about 0.01% to about 50% by weight of a nanozeolite; and (ii) the balance being conventional detergent ingredients selected from the group consisting of detersive surfactants, builders, buffers, bleaching compounds, bleach activators, chelating agents, anti-redeposition agents, dispersents, brightners, suds suppressers, hydrotropes, soil release agents, fabric softeners, filler salts, and mixtures thereof.

When applied in a uniform layer to a substrate, or via a laundry detergent product the nanozeolite composition adsorbs and greatly reduces many consumer negative odors while remaining undetectable to the human eye.

Nanozeolite

When uniformly delivered to the surface of a substrate, nanozeolites are invisible to the naked eye. Nanozeolites are those zeolites with crystallite sizes less than 300 nm which can thus be sprayed onto a variety of substrates, including fabrics, to provide malodor control benefits, without the visual negatives commonly associated with microsized inorganic sorbents. Nanozeolites also preferably have at least one pore system with pore sizes from about 3 to about 21 angstroms. Furthermore, the use of nanocrystalline zeolites provides an enhanced rate of odor removal, increased usable capacity and the ability to provide longer lasting odor control benefits (wet and dry state).

A nanozeolite is a zeolite with an individual crystallite size less than about 300 nanometers (nm), preferably less than about 200 nm, more preferably less than about 100 nm. Several crystallites may be aggregated to form a total particle of less than about 300 nm. Suitable zeolites fitting these characteristics include but are not limited to ZSM-5, silicalite, zeolite beta, zeolite Y, mordenite, and ferrierite. Specifically, colloidal silicalite, a hydrophobic zeolite belonging to the same structural class as ZSM-5, can be sprayed on dark substrates without any apparent whitening. Furthermore, the uniformity of the resulting thin film is much improved versus the equivalent micron sized particulates.

Preferably, nanozeolites for use in the present invention are hydrophobic. The hydrophobicity of a particular nanozeolites can be measured in terms of its Hydrophobicity Index (HI). An HI is calculated from the ratio of mass sorption of organic compound to mass sorption of water at specific partial pressures for the two adsorbates; thus $H_c = S_c/S_w$ for cyclohexane over water. Highly hydrophilic zeolites will have H values of less than 1.0. Highly hydrophobic zeolites will have H values substantially greater than 1.0. Selection of the adsorbent depends upon the pore opening of the zeolite structure of interest. It is well known that zeolites with 10-membered or less metal atoms ring openings will not adsorb substantial amounts of cyclohexane. For these zeolites, e.g. ZSM-5, ZSM-11, etc., n-hexane is a much more efficacious choice for the organic absorbent. Moreover, the partial pressure at which the adsorption is measure can have an effect on the absolute amount of adsorption of any component and also on the HI. For the purposes of defining the conditions at which the index is measure the following convention is used:

$H_{co7/o5}$ refers to an index where cyclohexane adsorption at 7 torr is referenced to water adsorption at 5 torr. Similarly, $H_{no7/o5}$ refers to an index wherein n-hexane adsorption at 7 torr is referenced to water adsorption at 5 torr. Zeolites suitable for use in the present invention will preferably have an $H_{no7/o5}$ greater than or equal to 1.

Manufacture of Nanozeolites

Nanozeolites according to the present invention can be prepared from commercial micron sized zeolites via wet milling techniques similar to those disclosed in U.S. Pat. No. 5,704,556. In a typical procedure, an aqueous dispersion of the micron sized zeolite is recirculated through a Netzsch media mill charged with Y-TZP media (yttria stabilized tetragonal polycrystals, 300 micron diameter). Total residence times, defined as the total time that each particle is in the mill, are typically between 30 seconds and 10 minutes to minimize loss of crystallinity. The particle size of the dispersion is monitored after each pass by conventional dynamic light scattering devices such as a Horiba LA-910. Depending on the specific nanozeolite to be prepared, media type, mill rpm, flow rate, milling time, batch volume and temperature can all be adjusted to achieve the desired particle size and crystallinity. For example, a 0.25% aqueous slurry of ZSM-5, with an average starting particle size of 3.2 microns and 30:1 molar ratio of silica to alumina (Zeolyst International, Valley Forge, Pa., was recycled through a media mill for a period of 10–15 minutes at a flow rate of 0.5 liter/minute to achieve an average particle size of less than 300 nm, by volume. Residual crystallinity was determined on a Scintag X1 powder x-ray diffractometer (Scintag, Inc., Cupertino, Calif. to be ~75% of the starting material.

Nanozeolites of the present invention can alternatively be prepared by the hydrolysis of TEOS with TPAOH as a template. The template TPAOH in the zeolite can be removed by the calcination at 550° C. for 5 hours. The separation and the emulsification of the primary particles can be achieved by the combination of the ultrasonic treatment and the adjustment of pH.

Liquid Carrier

In one embodiment of the present invention nanozeolites are delivered via an aqueous based composition. The dilute aqueous solution provides the maximum separation of nanozeolite molecules on the substrate and thereby maximizes the chance that an odor molecule will interact with a nanozeolite molecule.

The preferred carrier of the present invention is water. A highly preferred aqueous carrier composition comprises at least 50% water with the balance being made up of other conventional solvents such as ethanol. The water which is used can be distilled, deionized, or tap water. It has recently been discovered that water has an unexpected odor controlling effect of its own. It has been discovered that the intensity of the odor generated by some polar, low molecular weight organic amines, acids, and mercaptans is reduced when the odor-contaminated substrates are treated with an aqueous solution. Not to be bound by theory, it is believed that water solubilizes and depresses the vapor pressure of these polar, low molecular weight organic molecules, thus reducing their odor intensity.

Optional Ingredients

The odor absorbing composition of the present invention can also optionally provide a "scent signal" in the form of a pleasant odor which signals the removal of malodor from substrates. The scent signal is designed to provide a fleeting perfume scent, and is not designed to be overwhelming or to be used as an odor masking ingredient. When perfume is added as a scent signal, it is added only at very low levels, e.g., from about 0% to about 0.5%, preferably from about 0.003% to about 0.3%, more preferably from about 0.005% to about 0.2%, by weight of the usage composition.

Perfume can also be added as a more intense odor in product and on surfaces. When stronger levels of perfume are preferred, relatively higher levels of perfume can be added. Any type of perfume can be incorporated into the composition of the present invention. It is essential, however, that the perfume be added at a level wherein even if all of the perfume in the composition were to complex with the nanozeolite molecules, there will still be an effective level of uncomplexed nanozeolite molecules present in the solution to provide adequate odor control. In order to reserve an effective amount of nanozeolite molecules for odor control, perfume is typically present at a level wherein less than about 90% of the nanozeolite complexes with the perfume, preferably less than about 50% of the nanozeolite complexes with the perfume, more preferably, less than about 30% of the nanozeolite complexes with the perfume, and most preferably, less than about 10% of the nanozeolite complexes with the perfume. The nanozeolite to perfume weight ratio should be greater than about 8:1, preferably greater than about 10:1, more preferably greater than about 20:1, even more preferably greater than 40:1 and most preferably greater than about 70:1.

Preferably the perfume is hydrophilic and is composed predominantly of ingredients selected from two groups of ingredients, namely, (a) hydrophilic ingredients having a ClogP of less than about 3.5, more preferably less than about 3.0, and (b) ingredients having significant low detection threshold, and mixtures thereof. Typically, at least about 50%, preferably at least about 60%, more preferably at least about 70%, and most preferably at least about 80% by weight of the perfume is composed of perfume ingredients of the above groups (a) and (b). For these preferred perfumes, the nanozeolite to perfume weight ratio is typically of from about 2:1 to about 200:1; preferably from about 4:1 to about 100:1, more preferably from about 6:1 to about 50:1, and even more preferably from about 8:1 to about 30:1.

(a) Hydrophilic Perfume Ingredients

The hydrophilic perfume ingredients are more soluble in water, have less of a tendency to complex with the nanozeolites, and are more available in the odor absorbing composition than the ingredients of conventional perfumes. The degree of hydrophobicity of a perfume ingredient can be correlated with its octanol/water partition coefficient P. The octanol/water partition coefficient of a perfume ingredient is the ratio between its equilibrium concentration in octanol and in water. A perfume ingredient with a greater partition coefficient P is considered to be more hydrophobic. Conversely, a perfume ingredient with a smaller partition coefficient P is considered to be more hydrophilic. Since the partition coefficients of the perfume ingredients normally have high values, they are more conveniently given in the form of their logarithm to the base 10, logP. Thus the preferred perfume hydrophilic perfume ingredients of this invention have logP of about 3.5 or smaller, preferably of about 3.0 or smaller.

The logP of many perfume ingredients have been reported; for example, the Pomona92 database, available from Daylight Chemical Information Systems, Inc. (Daylight CIS), Irvine, Calif., contains many, along with citations to the original literature. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The ClogP values, which are the most reliable and widely used estimates for this physicochemical property, are used instead of the experimental logP values in the selection of perfume ingredients which are useful in the present invention.

Non-limiting examples of the more preferred hydrophilic perfume ingredients are allyl amyl glycolate, allyl caproate, amyl acetate, amyl propionate, anisic aldehyde, anisyl acetate, anisole, benzaldehyde, benzyl acetate, benzyl acetone, benzyl alcohol, benzyl formate, benzyl iso valerate, benzyl propionate, beta gamma hexenol, calone, camphor gum, laevo-carveol, d-carvone, laevo-carvone, cinnamic alcohol, cinnamyl acetate, cinnamic alcohol, cinnamyl formate, cinnamyl propionate, cis-jasmone, cis-3-hexenyl acetate, coumarin, cuminic alcohol, cuminic aldehyde, Cyclal C, cyclogalbanate, dihydroeuginol, dihydro isojasmonate, dimethyl benzyl carbinol, dimethyl benzyl carbinyl acetate, ethyl acetate, ethyl aceto acetate, ethyl amyl ketone, ethyl anthranilate, ethyl benzoate, ethyl butyrate, ethyl cinnamate, ethyl hexyl ketone, ethyl maltol, ethyl-2-methyl butyrate, ethyl methylphenyl glycidate, ethyl phenyl acetate, ethyl salicylate, ethyl vanillin, eucalyptol, eugenol, eugenyl acetate, eugenyl formate, eugenyl methyl ether, fenchyl alcohol, flor acetate (tricyclo decenyl acetate), fructone, frutene (tricyclo decenyl propionate), geraniol, geranyl oxyacetaldehyde, heliotropin, hexenol, hexenyl acetate, hexyl acetate, hexyl formate, hinokitiol, hydratropic alcohol, hydroxycitronellal, hydroxycitronellal diethyl acetal, hydroxycitronellol, indole, isoamyl alcohol, iso cyclo citral, isoeugenol, isoeugenyl acetate, isomenthone, isopulegyl acetate, isoquinoline, keone, ligustral, linalool, linalool oxide, linalyl formate, lyral, menthone, methyl acetophenone, methyl amyl ketone, methyl anthranilate, methyl benzoate, methyl benzyl acetate, methyl cinnamate, methyl dihydrojasmonate, methyl eugenol, methyl heptenone, methyl heptine carbonate, methyl heptyl ketone, methyl hexyl ketone, methyl isobutenyl tetrahydropyran, methyl-N-methyl anthranilate, methyl beta naphthyl ketone, methyl phenyl carbinyl acetate, methyl salicylate, nerol, nonalactone, octalactone, octyl alcohol (octanol-2), para-anisic aldehyde, para-cresol, para-cresyl methyl ether, para hydroxy phenyl butanone, para-methoxy acetophenone, para-methyl acetophenone, phenoxy ethanol, phenoxyethyl propionate, phenyl acetaldehyde, phenylacetaldehyde diethyl ether, phenylethyl oxyacetaldehyde, phenyl ethyl acetate, phenyl ethyl alcohol, phenyl ethyl dimethyl carbinol, prenyl acetate, propyl butyrate, pulegone, rose oxide, safrole, terpineol, vanillin, viridine, and mixtures thereof.

Nonlimiting examples of other preferred hydrophilic perfume ingredients which can be used in perfume compositions of this invention are allyl heptoate, amyl benzoate, anethole, benzophenone, carvacrol, citral, citronellol, citronellyl nitrile, cyclohexyl ethyl acetate, cymal, 4-decenal, dihydro isojasmonate, dihydro myrcenol, ethyl methyl phenyl glycidate, fenchyl acetate, florhydral, gamma-nonalactone, geranyl formate, geranyl nitrile, hexenyl isobutyrate, alpha-ionone, isobornyl acetate, isobutyl benzoate, isononyl alcohol, isomenthol, para-isopropyl phenylacetaldehyde, isopulegol, linalyl acetate, 2-methoxy naphthalene, menthyl acetate, methyl chavicol, musk ketone, beta naphthol methyl ether, neral, nonyl aldehyde, phenyl heptanol, phenyl hexanol, terpinyl acetate, Veratrol, yara-yara, and mixtures thereof.

The preferred perfume compositions used in the present invention contain at least 4 different hydrophilic perfume ingredients, preferably at least 5 different hydrophilic perfume ingredients, more preferably at least 6 different hydrophilic perfume ingredients, and even more preferably at least 7 different hydrophilic perfume ingredients. Most common perfume ingredients, which are derived from natural sources are composed of a multitude of components. When each such material is used in the formulation of the preferred perfume compositions of the present invention, it is counted as one single ingredient, for the purpose of defining the invention.

(b) Low Odor Detection Threshold Perfume Ingredient

The odor detection threshold of an odorous material is the lowest vapor concentration of that material which can be olfactorily detected. The odor detection threshold and some odor detection threshold values are discussed in, e.g., "Standardized Human Olfactory Thresholds", M. Devos et al, IRL Press at Oxford University Press, 1990, and "Compilation of Odor and Taste Threshold Values Data", F. A. Fazzalari, editor, ASTM Data Series DS 48A, American Society for Testing and Materials, 1978, both of said publications being incorporated by reference. The use of small amounts of perfume ingredients that have low odor detection threshold values can improve perfume odor character, even though they are not as hydrophilic as perfume ingredients of group (a) which are given hereinabove. Perfume ingredients that do not belong to group (a) above, but have a significantly low detection threshold, useful in the composition of the present invention, are selected from the group consisting of ambrox, bacdanol, benzyl salicylate, butyl anthranilate, cetalox, damascenone, alpha-damascone, gamma-dodecalactone, ebanol, herbavert, cis-3-hexenyl salicylate, alpha-ionone, beta-ionone, alpha-isomethylionone, lilial, methyl nonyl ketone, gamma-undecalactone, undecylenic aldehyde, and mixtures thereof. These materials are preferably present at low levels in addition to the hydrophilic ingredients of group (a), typically less than about 20%, preferably less than about 15%, more preferably less than about 10%, by weight of the total perfume compositions of the present invention. However, only low levels are required to provide an effect.

There are also hydrophilic ingredients of group (a) that have a significantly low detection threshold, and are especially useful in the composition of the present invention. Examples of these ingredients are allyl amyl glycolate, anethole, benzyl acetone, calone, cinnamic alcohol, coumarin, cyclogalbanate, Cyclal C, cymal, 4-decenal, dihydro isojasmonate, ethyl anthranilate, ethyl-2-methyl butyrate, ethyl methylphenyl glycidate, ethyl vanillin, eugenol, flor acetate, florhydral, fructone, frutene, heliotropin, keone, indole, iso cyclo citral, isoeugenol, lyral, methyl heptine carbonate, linalool, methyl anthranilate, methyl dihydrojasmonate, methyl isobutenyl tetrahydropyran, methyl beta naphthyl ketone, beta naphthol methyl ether, nerol, para-anisic aldehyde, para hydroxy phenyl butanone, phenyl acetaldehyde, vanillin, and mixtures thereof. Use of low odor detection threshold perfume ingredients minimizes the level of organic material that is released into the atmosphere.

The composition of the present invention can optionally contain adjunct odor-controlling materials, enzymes, chelating agents, antistatic agents, insect and moth repelling agents, colorants, especially bluing agents, antioxidants, and mixtures thereof in addition to the nanozeolite molecules. The total level of optional ingredients is low, preferably less than about 5%, more preferably less than about 3%, and even more preferably less than about 2%, by weight of the usage composition. These optional ingredients exclude the other ingredients specifically mentioned hereinbefore. Incorporating adjunct odor-controlling materials can enhance the capacity of the nanozeolite to control odors as well as broaden the range of odor types and molecule sizes, which can be controlled. Such materials include, for example, metallic salts, water-soluble cationic and anionic polymers, water-soluble bicarbonate salts, and mixtures thereof.

Some water-soluble polymers, e.g., water-soluble cationic polymer and water-soluble anionic polymers can be used in the composition of the present invention to provide additional odor control benefits.

a. Cationic Polymers. e.g., Polyamines

Water-soluble cationic Polymers, e.g., those containing amino functionalities, amido functionalities, and mixtures thereof, are useful in the present invention to control certain acid-type odors.

b. Anionic Polymers, e.g., Polyacrylic Acid

Water-soluble anionic polymers, e.g., polyacrylic acids and their water-soluble salts are useful in the present invention to control certain amine-type odors. Preferred polyacrylic acids and their alkali metal salts have an average molecular weight of less than about 20,000, more preferably less than 5,000. Polymers containing sulfonic acid groups, phosphoric acid groups, phosphonic acid groups, and their water-soluble salts, and mixtures thereof, and mixtures with carboxylic acid and carboxylate groups, are also suitable.

Water-soluble polymers containing both cationic and anionic functionalities are also suitable. Examples of these polymers are given in U.S. Pat. No. 4,909.986, issued Mar. 20, 1990 to N. Kobayashi and A. Kawazoe, incorporated herein by reference. Another example of water-soluble polymers containing both cationic and anionic functionalities is a copolymer of dimethyldiallyl ammonium chloride and acrylic acid, commercially available under the trade name Merquat 280° from Calgon.

When a water-soluble polymer is used it is typically present at a level of from about 0.001% to about 3%, preferably from about 0.005% to about 2%, more preferably from about 0.01% to about 1%, and even more preferably from about 0.05% to about 0.5%, by weight of the usage composition. (2). Soluble Carbonate and/or Bicarbonate Salts Water-soluble alkali metal carbonate and/or bicarbonate salts, such as sodium bicarbonate, potassium bicarbonate, potassium carbonate, cesium carbonate, sodium carbonate, and mixtures thereof can be added to the composition of the present invention in order to help to control certain acid-type odors. Preferred salts are sodium carbonate monohydrate, potassium carbonate, sodium bicarbonate, potassium bicarbonate, and mixtures thereof. When these salts are added to the composition of the present invention, they are typically present at a level of from about 0.1% to about 5%, preferably from about 0.2% to about 3%, more preferably from about 0.3% to about 2%, by weight of the composition. When these salts are added to the composition of the present invention it is preferably that incompatible metal salts not be present in the invention. Preferably, when these salts are used the composition should be essentially free of zinc and other incompatible metal ions, e.g., Ca, Fe, Ba, etc. which form water-insoluble salts.

Enzymes can be used to control certain types of malodor, especially malodor from urine and other types of excretions, including regurgitated materials. Proteases are especially desirable. The activity of commercial enzymes depends very much on the type and purity of the enzyme being considered. Enzymes that are water-soluble proteases like pepsin, tripsin, ficin, bromelin, papain, rennin, and mixtures thereof are particularly useful.

Enzymes are normally incorporated at levels sufficient to provide up to about 5 mg by weight, preferably from about 0.001 mg to about 3 mg, more preferably from about 0.002 mg to about 1 mg, of active enzyme per gram of the aqueous compositions. Stated otherwise, the aqueous compositions herein can comprise from about 0.0001% to about 0.5%, preferably from about 0.001% to about 0.3%, more preferably from about 0.005% to about 0.2% by weight of a commercial enzyme preparation. Protease enzymes are usually present in such commercial preparations at levels sufficient to provide from 0.0005 to 0.1 Anson units (AU) of activity per gram of aqueous composition.

Nonlimiting examples of suitable, commercially available, water soluble proteases are pepsin, tripsin, ficin, bromelin, papain, rennin, and mixtures thereof. Papain can be isolated, e.g., from papaya latex, and is available commercially in the purified form of up to, e.g., about 80% protein, or cruder, technical grade of much lower activity. Other suitable examples of proteases are the subtilisins which are obtained from particular strains of B. subtilis and B. licheniforms. Another suitable protease is obtained from a strain of Bacillus, having maximum activity throughout the pH range of 8–12, developed and sold by Novo Industries A/S under the registered trade name ESPERASE®. The preparation of this enzyme and analogous enzymes is described in British Patent Specification No. 1,243,784 of Novo. Proteolytic enzymes suitable for removing protein-based stains that are commercially available include those sold under the trade names ALCALASE® and SAVINASE® by Novo Industries A/S (Denmark) and MAXATASE® by International Bio-Synthetics, Inc. (The Netherlands). Other proteases include Protease A (see European Patent Application 130,756, published Jan. 9, 1985); Protease B (see European Patent Application Serial No. 87303761.8, filed Apr. 28, 1987, and European Patent Application 130,756, Bott et al, published Jan. 9, 1985); and proteases made by Genencor International, Inc., according to one or more of the following patents: Caldwell et al, U.S. Pat. Nos. 5,185,258, 5,204,015 and 5,244,791.

A wide range of enzyme materials and means for their incorporation into liquid compositions are also disclosed in U.S. Pat. No. 3,553,139, issued Jan. 5, 1971 to McCarty et al. Enzymes are further disclosed in U.S. Pat. No. 4,101,457, Place et al, issued Jul. 18, 1978, and in U.S. Pat. No. 4,507,219, Hughes, issued Mar. 26, 1985. Other enzyme materials useful for liquid formulations, and their incorporation into such formulations, are disclosed in U.S. Pat. No. 4,261,868, Hora et al, issued Apr. 14, 1981. Enzymes can be stabilized by various techniques, e.g., those disclosed and exemplified in U.S. Pat. No. 3,600,319, issued Aug. 17, 1971 to Gedge, et al., European Pat. Application Publication No. 0 199 405, Application No. 86200586.5, published Oct. 29, 1986, Venegas, and in U.S. Pat. No. 3,519,570. All of the above patents and applications are incorporated herein, at least in pertinent part.

Enzyme-polyethylene glycol conjugates are also preferred. Such polyethylene glycol (PEG) derivatives of enzymes, wherein the PEG or alkoxy-PEG moieties are coupled to the protein molecule through, e.g., secondary amine linkages. Suitable derivatization decreases immunogenicity, thus minimizes allergic reactions, while still maintains some enzymatic activity. An example of protease-PEG's is PEG-subtilisin Carlsberg from B. lichenniformis coupled to methoxy-PEGs through secondary amine linkage, and is available from Sigma-Aldrich Corp., St Louis, Mo. (4). Antistatic Agents The composition of the present invention can optionally contain an effective amount of antistatic agent to provide the treated clothes with in-wear static control. Preferred antistatic agents are those that are water soluble in at least an effective amount, such that the composition remains a clear solution, and are compatible with nanozeolites. Nonlimiting examples of these antistatic agents are polymeric quaternary ammonium salts, such as polymers conforming to the general formula: $[N(CH_3)_2-(CH_2)_3-NH-CO-NH-(CH_2)_3-N(CH_3)_2+-CH_2CH_2OCH_2CH_2]_x^2+2x[Cl^{31}]$ available under the trade name Mirapol A-15® from Rhone-Poulenc, and $[N(CH_3)_2-(CH_2)_3-NH-CO-(CH_2)_4-CO-NH-(CH_2)_3-N(CH_3)_2-(CH_2CH_2OCH_2CH_2]_x+x[Cl^{31}]$, available under the trade name Mirapol AD-1® from Rhone-Poulenc, quaternized polyethyleneimines, vinylpyrrolidone/methacrylamidopropyltrimethylammonium chloride copolymer, available under the trade name Gafquat HS-1000® from GAF; triethonium hydrolyzed collagen ethosulfate, available under the trade name Quat-Pro E® from Maybrook; neutralized sulfonated polystyrene, available, e.g., under the trade name Versa TL-130® from Alco Chemical, neutralized sulfonated styrene/maleic anhydride copolymers, available, e.g., under the trade name Versa TL-4® from Alco Chemical; polyethylene glycols; and mixtures thereof.

It is preferred that a no foaming, or low foaming, agent is used, to avoid foam formation during substrate treatment.

When an antistatic agent is used it is typically present at a level of from about 0.05% to about 10%, preferably from about 0.1% to about 5%, more preferably from about 0.3% to about 3%, by weight of the usage composition.

The composition of the present invention can optionally contain an effective amount of insect and/or moth repelling agents. Typical insect and moth repelling agents are pheromones, such as anti-aggregation pheromones, and other natural and/or synthetic ingredients. Preferred insect and moth repellent agents useful in the composition of the present invention are perfume ingredients, such as citronellol, citronellal, citral, linalool, cedar extract, geranium oil, sandalwood oil, 2-(diethylphenoxy)ethanol, 1-dodecene, etc. Other examples of insect and/or moth repellents useful in the composition of the present invention are disclosed in U.S. Pat. Nos. 4,449,987, 4,693,890, 4,696, 676, 4,933,371, 5,030,660, 5,196,200, and in "Semio Activity of Flavor and Fragrance Molecules on Various Insect Species", B. D. Mookheijee et al., published in Bioactive Volatile Compounds from Plants, ASC Symposium Series 525, R. Teranishi, R. G. Buttery, and H. Sugisawa, 1993, pp. 35–48, all of said patents and publications being incorporated herein by reference. When an insect and/or moth repellent is used it is typically present at a level of from about 0.005% to about 3%, by weight of the usage composition.

Colorants and dyes, especially bluing agents, can be optionally added to the odor absorbing compositions for visual appeal and performance impression. When colorants are used, they are used at extremely low levels to avoid substrate staining. Preferred colorants for use in the present compositions are highly water-soluble dyes, e.g., Liquitint® dyes available from Milliken Chemical Co. Non-limiting examples of suitable dyes are, Liquitint Blue HP®, Liquitint Blue 65®, Liquitint Pat. Blue®, Liquitint Royal Blue®, Liquitint Experimental Yellow 8949-43®, Liquitint Green HMC®, Liquitint Yellow II®, and mixtures thereof, preferably Liquitint Blue HP®, Liquitint Blue 65®, Liquitint Patent Blue®, Liquitint Royal Blue®, Liquitint Experimental Yellow 8949-43®, and mixtures thereof.

Optionally, but preferably, solubilized, water-soluble, antimicrobial preservative can be added to the composition of the present invention if the antimicrobial material C. is not sufficient, or is not present. Contamination by certain microorganisms with subsequent microbial growth can result in an unsightly and/or malodorous solution.

It is preferable to use a broad spectrum preservative, e.g., one that is effective on both bacteria (both gram positive and gram negative) and fungi. A limited spectrum preservative, e.g., one that is only effective on a single group of microorganisms, e.g., fungi, can be used in combination with a broad spectrum preservative or other limited spectrum preservatives with complimentary and/or supplementary activity. A mixture of broad spectrum preservatives can also be used. In some cases where a specific group of microbial contaminants is problematic (such as Gram negatives), aminocarboxylate chelators may be used alone or as potentiators in conjunction with other preservatives. These chelators which include, e.g., ethylenediaminetetraacetic acid (EDTA), hydroxyethylenediaminetriacetic acid, diethylenetriaminepentaacetic acid, and other aminocarboxylate chelators, and mixtures thereof, and their salts, and mixtures thereof, can increase preservative effectiveness against Gram-negative bacteria, especially Pseudomonas species.

Antimicrobial preservatives useful in the present invention include biocidal compounds, i.e., substances that kill microorganisms, or biostatic compounds, i.e., substances that inhibit and/or regulate the growth of microorganisms.

Preferred antimicrobial preservatives are those that are water-soluble and are effective at low levels because the organic preservatives can form inclusion complexes with the nanozeolite molecules and compete with the malodorous molecules for the nanozeolite cavities, thus rendering the nanozeolite ineffective as odor controlling actives. Water-soluble preservatives useful in the present invention are those that have a solubility in water of at least about 0.3 g per 100 ml of water, i.e., greater than about 0.3% at room temperature, preferably greater than about 0.5% at room temperature. These types of preservatives have a lower affinity to the nanozeolite cavity, at least in the aqueous phase, and are therefore more available to provide antimicrobial activity. Preservatives with a water-solubility of less than about 0.3% and a molecular structure that readily fits into the nanozeolite cavity, have a greater tendency to form inclusion complexes with the nanozeolite molecules, thus rendering the preservative less effective to control microbes in the nanozeolite solution. Therefore, many well known preservatives such as short chain alkyl esters of p-hydroxybenzoic acid, commonly known as parabens; N-(4-chlorophenyl)-N'-(3,4-dichlorophenyl) urea, also known as 3,4,4'-trichlorocarbanilide or triclocarban; 2,4,4'-trichloro-2'-hydroxy diphenyl ether, commonly known as triclosan are not preferred in the present invention since they are relatively ineffective when used in conjunction with nanozeolite.

The water-soluble antimicrobial preservative in the present invention is included at an effective amount. The term "effective amount" as herein defined means a level sufficient to prevent spoilage, or prevent growth of inadvertently added microorganisms, for a specific period of time. In other words, the preservative is not being used to kill microorganisms on the surface onto which the composition is deposited in order to eliminate odors produced by microorganisms. Instead, it is preferably being used to prevent spoilage of the nanozeolite solution in order to increase the shelf-life of the composition. Preferred levels of preservative are from about 0.0001% to about 0.5%, more preferably from about 0.0002% to about 0.2%, most preferably from about 0.0003% to about 0.1%, by weight of the usage composition.

In order to reserve most of the nanozeolites for odor control, the nanozeolite to preservative molar ratio should be greater than about 5:1, preferably greater than about 10:1, more preferably greater than about 50:1, even more preferably greater than about 100:1.

The preservative can be any organic preservative material, which will not cause damage to substrate appearance, e.g., discoloration, coloration, bleaching. Preferred water-soluble preservatives include organic sulfur compounds, halogenated compounds, cyclic organic nitrogen compounds, low molecular weight aldehydes, quaternary ammonium compounds, dehydroacetic acid, phenyl and phenolic compounds, and mixtures thereof.

The composition of the present invention can also be used in an article of manufacture comprising said composition plus a spray dispenser. When the commercial embodiment of the article of manufacture is used, it is optional, but preferable, to include the preservative. Therefore, the most basic article of manufacture comprises nanozeolites, a carrier, and a spray dispenser.

The article of manufacture can also comprise the composition of the present invention in a container in association with a set of instructions to use the composition in an amount effective to provide a solution to problems involving and/or provision of a benefit related to those selected from the group consisting of: killing or reducing the level of, microorganisms; reduction in odors. It is important that the consumer be aware of these additional benefits, since otherwise the consumer would not know that the composition would solve these problems and/or provide these benefits.

As used herein, the phrase "in association with" means the set of instructions are either directly printed on the container itself or presented in a separate manner including, but not limited to, a brochure, print advertisement, electronic advertisement, and/or verbal communication, so as to communicate the set of instructions to a consumer of the article of manufacture. The set of instructions preferably comprises the instruction to apply an effective amount of the composition, preferably by spraying, to provide the indicated benefit, e.g., anti-microbial action, and/or anti-static effect and, optionally the provision of the main effect of odor control and/or reduction.

The article of manufacture herein comprises a spray dispenser. The nanozeolite composition is placed into a spray dispenser in order to be distributed onto the substrate. Said spray dispenser is preferably any of the manually activated means for producing a spray of liquid droplets as is known in the art, e.g. trigger-type, pump-type, non-aerosol self-pressurized, and aerosol-type spray means. The spray dispenser herein does not normally include those that will substantially foam the clear, aqueous odor absorbing composition. It has been found that the performance is increased by providing smaller particle droplets.

The spray dispenser can be an aerosol dispenser. Said aerosol dispenser comprises a container which can be constructed of any of the conventional materials employed in fabricating aerosol containers. The dispenser must be capable of withstanding internal pressure in the range of from about 20 to about 110 p.s.i.g., more preferably from about 20 to about 70 p.s.i.g. The one important requirement concerning the dispenser is that it be provided with a valve member which will permit the clear, aqueous odor absorbing composition contained in the dispenser to be dispensed in the form of a spray of very fine, or finely divided, particles or droplets. The aerosol dispenser utilizes a pressurized sealed container from which the clear, aqueous odor-absorbing composition is dispensed through a special actuator/valve assembly under pressure. The aerosol dispenser is pressurized by incorporating therein a gaseous component generally known as a propellant. Common aerosol propellants, e.g., gaseous hydrocarbons such as isobutane, and mixed halogenated hydrocarbons, which are not preferred. Halogenated hydrocarbon propellants such as chlorofluoro hydrocarbons have been alleged to contribute to environmental problems. Hydrocarbon propellants can form complexes with the nanozeolite molecules thereby reducing the availability of nanozeolite molecules for odor absorption. Preferred propellants are compressed air, nitrogen, inert gases, carbon dioxide, etc. A more complete description of commercially available aerosol-spray dispensers appears in U.S. Pat. No. 3,436,772, Stebbins, issued Apr. 8, 1969; and U.S. Pat. No. 3,600,325, Kaufman et al., issued Aug. 17, 1971; both of said references are incorporated herein by reference.

Preferably the spray dispenser can be a self-pressurized non-aerosol container having a convoluted liner and an elastomeric sleeve. Said self-pressurized dispenser comprises a liner/sleeve assembly containing a thin, flexible radially expandable convoluted plastic liner of from about 0.010 to about 0.020 inch thick, inside an essentially cylindrical elastomeric sleeve. The liner/sleeve is capable of holding a substantial quantity of odor-absorbing fluid product and of causing said product to be dispensed. A more complete description of self-pressurized spray dispensers can be found in U.S. Pat. No. 5,111,971, Winer, issued May 12, 1992, and U.S. Pat. No. 5,232,126, Winer, issued Aug. 3, 1993; both of said references are herein incorporated by reference. Another type of aerosol spray dispenser is one wherein a barrier separates the odor absorbing composition from the propellant (preferably compressed air or nitrogen), as disclosed in U.S. Pat. No. 4,260,110, issued Apr. 7, 1981, and incorporated herein by reference. Such a dispenser is available from EP Spray Systems, East Hanover, N.J.

More preferably, the spray dispenser is a non-aerosol, manually activated, pump-spray dispenser. Said pump-spray dispenser comprises a container and a pump mechanism which securely screws or snaps onto the container. The container comprises a vessel for containing the aqueous odor-absorbing composition to be dispensed.

The pump mechanism comprises a pump chamber of substantially fixed volume, having an opening at the inner end thereof. Within the pump chamber is located a pump stem having a piston on the end thereof disposed for reciprocal motion in the pump chamber. The pump stem has a passageway there through with a dispensing outlet at the outer end of the passageway and an axial inlet port located inwardly thereof.

The container and the pump mechanism can be constructed of any conventional material employed in fabricating pump-spray dispensers, including, but not limited to: polyethylene; polypropylene; polyethyleneterephthalate; blends of polyethylene, vinyl acetate, and rubber elastomer. A preferred container is made of clear, e.g., polyethylene terephthalate. Other materials can include stainless steel. A more complete disclosure of commercially available dispensing devices appears in: U.S. Pat. No. 4,895,279, Schultz, issued Jan. 23, 1990; U.S. Pat. No. 4,735,347, Schultz et al., issued Apr. 5, 1988; and U.S. Pat. No. 4,274,560, Carter, issued Jun. 23, 1981; all of said references are herein incorporated by reference.

Most preferably, the spray dispenser is a manually activated trigger-spray dispenser. Said trigger-spray dispenser comprises a container and a trigger both of which can be constructed of any of the conventional material employed in fabricating trigger-spray dispensers, including, but not limited to: polyethylene; polypropylene; polyacetal; polycarbonate; polyethyleneterephthalate; polyvinyl chloride; polystyrene; blends of polyethylene, vinyl acetate, and rubber elastomer. Other materials can include stainless steel and glass. A preferred container is made of clear, e.g. polyethylene terephthalate. The trigger-spray dispenser does not incorporate a propellant gas into the odor-absorbing composition, and preferably it does not include those that will foam the odor-absorbing composition. The trigger-spray dispenser herein is typically one which acts upon a discrete amount of the odor-absorbing composition itself, typically by means of a piston or a collapsing bellows that displaces the composition through a nozzle to create a spray of thin liquid. Said trigger-spray dispenser typically comprises a pump chamber having either a piston or bellows which is movable through a limited stroke response to the trigger for varying the volume of said pump chamber. This pump chamber or bellows chamber collects and holds the product for dispensing. The trigger spray dispenser typically has an outlet check valve for blocking communication and flow of fluid through the nozzle and is responsive to the pressure inside the chamber. For the piston type trigger sprayers, as the trigger is compressed, it acts on the fluid in the chamber and the spring, increasing the pressure on the fluid. For the bellows spray dispenser, as the bellows is compressed, the pressure increases on the fluid. The increase in fluid pressure in either trigger spray dispenser acts to open the top outlet check valve. The top valve allows the product to be forced through the swirl chamber and out the nozzle to form a discharge pattern. An adjustable nozzle cap can be used to vary the pattern of the fluid dispensed.

For the piston spray dispenser, as the trigger is released, the spring acts on the piston to return it to its original position. For the bellows spray dispenser, the bellows acts as the spring to return to its original position. This action causes a vacuum in the chamber. The responding fluid acts to close the outlet valve while opening the inlet valve drawing product up to the chamber from the reservoir.

A more complete disclosure of commercially available dispensing devices appears in U.S. Pat. No. 4,082,223, Nozawa, issued Apr. 4, 1978; U.S. Pat. No. 4,161, 288, McKinney, issued Jul. 17, 1985; U.S. Pat. No. 4,434,917, Saito et al., issued Mar. 6, 1984; and U.S. Pat. No. 4,819, 835, Tasaki, issued Apr. 11, 1989; U.S. Pat. No. 5,303,867, Peterson, issued Apr. 19, 1994; all of said references are incorporated herein by reference.

A broad array of trigger sprayers or finger pump sprayers are suitable for use with the compositions of this invention. These are readily available from suppliers such as Calmar, Inc., City of Industry, Calif.; CSI (Continental Sprayers, Inc.), St. Peters, Mo.; Berry Plastics Corp., Evansville, Ind., a distributor of Guala® sprayers; or Seaquest Dispensing, Cary, Ill.

The preferred trigger sprayers are the blue inserted Guala® sprayer, available from Berry Plastics Corp., or the Calmar TS800-1A®, TS1300®, and TS-800-2®, available from Calmar Inc., because of the fine uniform spray characteristics, spray volume, and pattern size. More preferred are sprayers with precompression features and finer spray characteristics and even distribution, such as Yoshino sprayers from Japan. Any suitable bottle or container can be used with the trigger sprayer, the preferred bottle is a 17 fl-oz. bottle (about 500 ml) of good ergonomics similar in shape to the Cinch® bottle. It can be made of any materials such as high density polyethylene, polypropylene, polyvinyl chloride, polystyrene, polyethylene terephthalate, glass, or any other material that forms bottles. Preferably, it is made of high density polyethylene or clear polyethylene terephthalate.

For smaller fluid ounce sizes (such as 1 to 8 ounces), a finger pump can be used with canister or cylindrical bottle. The preferred pump for this application is the cylindrical Euromist II® from Seaquest Dispensing. More preferred are those with precompression features.

Malodor Control Testing

Malodor control effectiveness testing is conducted against three commonly encountered environmental malodors: cigarette smoke, bacon grease odor and synthetic body odor. Panelists evaluate the relative malodor control performance of various hydrophobic nanozeolites against a control sample. Testing is conducted as follows.

Fabric Preparation

Terry wash cloths (86% cotton/14% polyester) are stripped by washing them twice with 65 g of a perfume free laundry detergent (e.g., Tide-Free® sold by the Procter & Gamble Co.), followed by two cycles without detergent, all in 120° F. water with 0 gpg hardness. The terries are machine dried on the cotton/high setting for 90 min. with a ten minute cool-down. Terries are stored in a sealed plastic container until needed, and are then cut into quarters (5.5" square) for use in testing.

Malodor Exposure (a) Bacon Grease. The malodor chamber consists of a 12 gal. galvanized trash can which is modified with a hole drilled into the side for the purpose of passing through the electrical power cord of a hot plate. The lid of the can is modified with a hanging carousel and manual rotator so that a maximum of 4 test fabrics can be safely suspended and rotated within the can when sealed.

Test swatches are hung from the carousel hanger in the lid. The contents of 1–2 oz. jar of Bacon Grease Composite (Empirical Manufacturing Co.) are emptied into an aluminum baking dish which is placed on a pre-heated hot plate at the bottom of the malodor chamber. For 5 minutes, the bacon grease is allowed to melt and heat to 250° F. The lid is then placed on the chamber and the carousel is rotated at approximately 15 RPM for exactly 3 minutes before the swatches are removed.

(b) Cigarette Smoke. One standard cigarette is lit and placed in an ashtray at the bottom of the malodor chamber. After one minute, the lid (with test swatches hanging from carousel) is placed on the chamber. The carousel is rotated at approximately 15 RPM, and the swatches are removed after 1 minute.

(c) Body Odor. Exactly 250l of a 0.1% solution of artificial body soil in ethanol is uniformly applied to the entire surface area of each swatch. The swatches are placed in mylar bags, sealed with tape and allowed to equilibrate overnight.

Treatment

Following removal from the mylar bag, six sprays of aqueous test solution (1% active) are applied to each swatch using a trigger sprayer. The swatches are then line dried in an odor free room for 1 hour. Following drying, each swatch is graded by a trained odor evaluator.

EXAMPLES

The following examples are included to illustrate several embodiments of the present invention while not limiting to said examples.

Examples 1–6

Granular laundry detergents for use in domestic appliances or handwashing of laundry at from 100 to 10,000 ppm, depending on appliance and/or water and/or conditions, are prepared in accordance with the invention:

| Ingredient% | 1 | 2 | 3 | 4 | 5 | 6 |
|---|---|---|---|---|---|---|
| LAS (0–35) | 4 | — | 10 | 20 | 30 | 35 |
| Alkyl Sulfate (0–20) | 10 | 3 | 1 | — | — | — |
| Alkyl Alkoxy Sulfate (0–5) | — | — | 0.5 | — | 5 | — |
| Nonionic (0–15) | 5 | 10 | 2 | 0.5 | 1 | — |
| Glucamide (0–5) | 3 | 1 | — | — | — | — |
| Amine Oxide (0–2) | 0.5 | — | — | 2 | — | — |
| QAS (0–2) | — | — | — | — | 1.8 | 2 |
| nanozeolites | 1 | .01 | 25 | 10 | 30 | 5 |
| Conventional Zeolites | — | 20 | — | — | — | — |
| Carbonate (0–30) | 10 | 10 | 5 | 15 | — | 20 |
| Phosphates (0–30) | — | — | — | — | — | 20 |
| Silicate system (0–20) | 5 | 1 | 3 | — | 2 | 10 |
| Non-polymer type polycarboxylate (0–20) | — | — | 5 | — | 5 | — |
| Polymer-type polycarboxylate (0–20) | 1 | 5 | — | 10 | 4 | — |
| Carbohydrate anti-redeposition agent (0–10) | 0.1 | 0.2 | 5 | 0.3 | 0.2 | — |
| Primary Oxygen Bleach (0–20) | 20 | 15 | 10 | 5 | 3 | — |
| Hydrophilic Bleach Activator (0–10) | — | 2 | — | — | 4 | 2 |
| Hydrophobic Bleach Activator (0–10) | — | 2 | 1 | — | 5 | — |
| Organic Bleach Booster (0–5) | — | — | — | 2 | — | — |
| Transition-metal bleach catalyst (0–10,000 ppm) | 10 | 100 | 1000 | — | 50 | 10000 |
| Photobleach (0–1000 ppm) | — | — | 10 | — | 5 | — |
| Chelant System (0–3) | 2 | 1 | 0.5 | 3 | 1 | 0 |
| Enzyme System (0–8) | 8 | — | 3 | 4 | 6 | 1 |
| Brightener (0–2) | 0.1 | 0.1 | 0.1 | 0.2 | 0.3 | 1 |
| Soil Release Agent (0–5) | — | 0.1 | 1 | 2 | — | 0.3 |
| Perfume (0–5) | 0.01 | 0.1 | — | 3 | 2 | 1 |
| Antifoam system (0–5) | 0.05 | 0.1 | 0.2 | 0.5 | 0.7 | — |
| Sulfate, stabilizers, process aids, minors to | 100% | 100% | 100% | 100% | 100% | 100% |
| Density in g/liter (range) | 200–900 | 200–900 | 200–900 | 200–900 | 200–900 | 200–900 |

Examples 7–13

| Ingredients | 7 | 8 | 9 | 10 | 11 | 12 | 13 |
|---|---|---|---|---|---|---|---|
| Total surfactant[1]: | 22.5 | 19.4 | 20.3 | 18.2 | 20.4 | 19.1 | 22.3 |
| sodium sulfate | 14.4 | 8.9 | — | 10.2 | 8.0 | 8.9 | 8.9 |
| sodium carbonate | 26.2 | 16.0 | 30.4 | 14.3 | 15.2 | 15.0 | 16.0 |
| citric acid | — | 3.5 | — | — | 7.0 | 4.0 | 3.5 |
| zeolite A | — | 26.3 | 20.5 | 21.0 | 12.0 | 20.0 | 25.2 |
| poly acrylate 4500 | — | 3.2 | — | — | 4.7 | 3.2 | 3.2 |
| sodium silicate | 1.2 | 0.6 | — | — | — | 1.0 | 0.6 |
| soil release agent | 0.6 | — | — | 1.1 | 3.0 | — | — |
| nanozeolite | 25 | 5 | .01 | 1 | 15 | 5 | 10 |
| Balance adjunct ingredients to 100% | | | | | | | |

-continued

| Ingredients | 7 | 8 | 9 | 10 | 11 | 12 | 13 |

[1]The Total Surfactants may comprise alkyl benzene sulfonates, linear alkyl sulfonates, NEODOL45-7, alkyl ethoxylates, alcohol ethoxylates, branched chain alkyl sulfonates and alkyl ethoxy sulfonates.

Use of these detergent compositions comprising nanozeolites to wash substrates in need of malodor control substantially reduces the malodor associated with the substrate following exposure to various sources of malodor.

Examples 14–18

| Ingredient | 14 | 15 | 16 | 17 | 18 |
|---|---|---|---|---|---|
| DI Water | Balance | Balance | Balance | Balance | Balance |
| Nanozeolite | 0.05 | 1 | 5 | 10 | 5 |
| Polyacrylic acid | 0.10 | — | 0.10 | — | — |
| Diethylene glycol | 0.38 | 0.38 | — | — | — |
| Wetting Agent | 0.10 | 0.10 | — | — | — |
| Ethanol | 3.00 | — | — | — | — |
| Perfume | 0.12 | — | 0.12 | — | 0.12 |

What is claimed is:

1. A composition for controlling malodor on a substrate comprising:
    a. from about 0.05% to about 10% of a hydrophobic nanozeolite having a silica to alumina molar ratio of at least 10:1;
    b. from about 90% to about 99.95% of a compatible carrier; and
    c. optionally additional ingredients selected from the group consisting of surfactants, perfumes, preservatives, anti-microbials, de-foaming agents, antifoaming agents, bacteriocides, fungicides, antistatic agents, insect and moth repellents, colorants, bluing agents, antioxidants and mixtures thereof.

2. A composition according to claim 1 wherein at least 50% of the nanozeolite has a particle size of less than 200 nm.

3. A composition according to claim 1 wherein the nanozeolite has a hydrophobicity index, $H_{n07/o5}$, of at least 1.

4. A composition according to claim 1 wherein the nanozeolite has a silica to alumina molar ratio of at least 60:1.

5. A composition according to claim 1 wherein the nanozeolite has a silica to alumina molar ratio of at least 100:1.

6. A composition according to claim 1 wherein the nanozeolite is selected from the group consisting of ZSM-5, silicalite, zeolite beta, zeolite Y, mordenite, ferrierite and mixtures thereof.

7. A composition according to claim 1 wherein at least 50% of the nanozeolite has a particle size of less than 200 nm.

8. A composition according to claim 1 wherein at least 50% of the nanozeolite has a particle size of less than 100 nm.

9. A composition according to claim 1 wherein the suitable carrier is water.

10. A laundry detergent composition for controlling malodor on a substrate comprising:
    a. from about 0.1% to about 50% of a hydrophobic nanozeolite having a silica to alumina molar ratio of at least 10:1; and
    b. a balance of conventional detergent ingredients selected from the group consisting of surfactants, builders, chelants, brighteners, bleaching agents, enzymes, soil release polymers, dye transfer inhibitors, fillers, perfumes and mixtures thereof.

11. A laundry detergent composition according to claim 10 wherein at least 50% of the nanozeolite has a particle size of less than 300 nm.

12. A laundry detergent composition according to claim 10 wherein at least 50% of the nanozeolite has a particle size of less than 200 nm.

13. A laundry detergent composition according to claim 10 wherein at least 50% of the nanozeolite has a particle size of less than 100 nm.

14. A laundry detergent composition according to claim 10 wherein the nanozeolite has a hydrophobicity index, $H_{n07/o5}$, of at least 1.

15. A laundry detergent composition according to claim 10 wherein the nanozeolite has a silica to alumina molar ratio of at least 60:1.

16. A laundry detergent composition according to claim 10 wherein the nanozeolite has a silica to alumina molar ratio of at least 100:1.

17. A laundry detergent composition according to claim 10 wherein the nanozeolite is selected from the group consisting of ZSM-5, silicalite, zeolite beta, zeolite Y, mordenite, ferrierite and mixtures thereof.

18. A method for removing malodor from a porous substrate, the method comprising the steps of
    (A) applying to said substrate a composition comprising:
        (i) from about 0.05% to about 10% by weight of a hydrophobic nanozeolite having a silica to alumina molar ratio of at least 10:1:
        (ii) from about 90% to about 99.95% by weight of a compatible carrier; and
        (iii) optionally additional ingredients selected from the group consisting of surfactants, perfumes, preservatives, anti-microbial, de-foaming agents, antifoaming agents, bacteriocides, fungicides, antistatic agents, insect and moth repellents, colorants, bluing agents, antioxidants and mixtures thereof; and
    (B) allowing the substrate to dry.

19. A method for removing malodor according to claim 18 wherein at least 50% of the nanozeolite has a particle size of less than 300 nm.

20. A method for removing malodor according to claim 18 wherein at least 50% of the nanozeolite has a particle size of less than 200 nm.

21. A method for removing malodor according to claim 18 wherein at least 50% of the nanozeolite has a particle size of less than 100 nm.

22. A method for removing malodor according to claim 18 wherein the nanozeolite has a silica to alumina molar ratio of at least 60:1.

23. A method for removing malodor according to claim 18 wherein the nanozeolite has a silica to alumina molar ratio of at least 100:1.

24. A method according to claim 18 wherein the nanozeolite is selected from the group consisting of ZSM-5, silicalite, zeolite beta, zeolite Y, mordenite, ferrierite and mixtures thereof.

25. A method according to claim 18 wherein the liquid carrier is water.

26. An article of manufacture comprising:
    (a) a spray bottle; and
    (b) a composition comprising:
        (i) from about 0.05% to about 10% by weight of a hydrophobic nanozeolite having a silica to alumina molar ratio of at least 10:1;

(ii) from about 90% to about 99.95% by weight of a liquid carrier; and (iii) optionally additional ingredients selected from the group consisting of surfactants, perfumes, preservatives, anti-microbials, de-foaming agents, antifoaming agents, bacteriocides, fungicides, anti-static agents, insect and moth repellents, colorants, bluing agents, antioxidants and mixtures thereof.

27. An article of manufacture comprising:

(a) a spray bottle;

(b) a composition comprising:

(i) from about 0.05% to about 10% by weight of a hydrophobic nanozeolite having a silica to alumina molar ratio of at least 10:1;

(ii) from about 90% to about 99.95% by weight of a liquid carrier; and (iii) optionally additional ingredients selected from the group consisting of surfactants, perfumes, preservatives, anti-microbials, de-foaming agents, antifoaming agents, bacteriocides, fungicides, anti-static agents, insect and moth repellent, colorants, bluing agents, antioxidants and mixtures thereof; and (c) a set of instructions in association with said spray bottle, detailing use of the composition in an amount effective to provide reduction in odors on a porous substrate.

* * * * *